(12) United States Patent
Quinn et al.

(10) Patent No.: US 10,517,763 B2
(45) Date of Patent: Dec. 31, 2019

(54) SYSTEM AND METHOD FOR PROTECTIVE EYEWEAR

(71) Applicant: TIDI Products, LLC, Neenah, WI (US)

(72) Inventors: Charles Quinn, Sun Prairie, WI (US); Brian L. Wilt, Appleton, WI (US); Michael A. Andrew, Monona, WI (US)

(73) Assignee: TIDI Products, LLC, Neenah, WI (US)

( * ) Notice: Subject to any disclaimer, the term of this patent is extended or adjusted under 35 U.S.C. 154(b) by 185 days.

(21) Appl. No.: 15/519,255

(22) PCT Filed: Oct. 19, 2015

(86) PCT No.: PCT/US2015/056212
§ 371 (c)(1),
(2) Date: Apr. 14, 2017

(87) PCT Pub. No.: WO2016/064731
PCT Pub. Date: Apr. 28, 2016

(65) Prior Publication Data
US 2017/0239089 A1  Aug. 24, 2017

Related U.S. Application Data

(60) Provisional application No. 62/067,589, filed on Oct. 23, 2014.

(51) Int. Cl.
*A61F 9/02* (2006.01)
*G02C 1/04* (2006.01)
*G02C 5/22* (2006.01)
*B65D 83/08* (2006.01)
*A42B 3/18* (2006.01)
(Continued)

(52) U.S. Cl.
CPC .......... *A61F 9/025* (2013.01); *B65D 83/0805* (2013.01); *G02C 1/04* (2013.01);
(Continued)

(58) Field of Classification Search
CPC .......... A42B 1/247; A42B 3/04; A42B 3/185; A42B 3/20; A61F 9/025; A61F 9/02;
(Continued)

(56) References Cited

U.S. PATENT DOCUMENTS 2,060,127 A  * 11/1936 Schofield ................ G02C 7/16
                                                                 2/12
2,758,506 A  *  8/1956 McNeill .................. G02C 9/02
                                                                 2/13
(Continued)

FOREIGN PATENT DOCUMENTS

EP       0128735 A2   12/1984
FR       2449901 A     9/1980

*Primary Examiner* — Khaled Annis
*Assistant Examiner* — Dakota Marin
(74) *Attorney, Agent, or Firm* — Boyle Fredrickson, S.C.

(57) ABSTRACT

A flip-to-wear eye shield system is provided. By integrating a hinge into elements of the frame and/or the lens, the eye shield can be manufactured and assembled more quickly and with less costs. In an embodiment, a lens may click (or snap) onto molded posts of a frame in a substantially flat position. An integrated living hinge in the frame may bend to allow the lens to flip downwards toward the frame to a second position for use. The posts may also click (or snap) into place in an underside of the frames. In another embodiment, a lens may click (or snap) onto molded posts of a flame in a substantially flat position. An integrated living hinge, formed by notches in the lens, may allow the lens to bend to flip downwards to the frame to a second position for use. A dispenser allows storing the eye shields in the flat position and dispensing in the second position for use.

13 Claims, 8 Drawing Sheets

(51) Int. Cl.
  *A42B 3/04*   (2006.01)
  *A42B 3/20*   (2006.01)
  *A42B 1/24*   (2006.01)
  *A61F 9/06*   (2006.01)
  *G02C 9/02*   (2006.01)

(52) U.S. Cl.
  CPC ............ *G02C 5/2263* (2013.01); *A42B 1/247* (2013.01); *A42B 3/04* (2013.01); *A42B 3/185* (2013.01); *A42B 3/20* (2013.01); *A61F 9/02* (2013.01); *A61F 9/026* (2013.01); *A61F 9/029* (2013.01); *A61F 9/061* (2013.01); *G02C 5/22* (2013.01); *G02C 5/2209* (2013.01); *G02C 9/02* (2013.01); *G02C 2200/08* (2013.01)

(58) Field of Classification Search
  CPC .......... A61F 9/026; A61F 9/029; A61F 9/061; G02C 1/04; G02C 5/2263; G02C 5/22; G02C 5/2209; G02C 9/02; G02C 2200/08
  USPC ..................... 2/439, 438, 443, 451
  See application file for complete search history.

(56) References Cited

U.S. PATENT DOCUMENTS

| | | | |
|---|---|---|---|
| 3,383,155 A | 5/1968 | Bourke | |
| 3,383,707 A * | 5/1968 | McNeill | G02C 9/02 2/12 |
| 4,322,138 A | 3/1982 | Minart | |
| 4,759,622 A * | 7/1988 | Schmidthaler | G02C 1/06 351/86 |
| 4,887,895 A * | 12/1989 | Tzeng | G02C 5/08 351/63 |
| 5,335,025 A * | 8/1994 | Wang | G02C 7/10 2/13 |
| 5,457,503 A | 10/1995 | Chen | |
| 5,768,716 A | 6/1998 | Porsche | |
| 5,771,499 A * | 6/1998 | Monaco | A61F 9/026 2/428 |
| 6,869,180 B1 * | 3/2005 | Kidouchim | G02C 9/00 351/47 |
| 7,244,023 B1 * | 7/2007 | Hsiao | G02C 9/00 351/47 |
| 7,661,815 B2 * | 2/2010 | Lipawsky | G02C 9/00 351/47 |
| 2005/0268384 A1 | 12/2005 | Hartman | |
| 2009/0086156 A1 | 4/2009 | Salk | |
| 2009/0188015 A1 * | 7/2009 | Grad | A61F 9/025 2/15 |
| 2011/0007262 A1 * | 1/2011 | Taylor | G02C 1/04 351/60 |
| 2011/0296575 A1 | 12/2011 | Shaw | |
| 2012/0272437 A1 | 11/2012 | Grad et al. | |
| 2015/0173953 A1 * | 6/2015 | Wang | A61F 9/04 128/858 |

* cited by examiner

SYSTEM AND METHOD FOR PROTECTIVE EYEWEAR

CROSS-REFERENCE TO RELATED APPLICATIONS

The present international application is a 371 U.S. National Phase Entry of PCT/US15/56212, which has an international filing date of Oct. 19, 2015, which claims the benefit of U.S. App. No. 62/067,589 filed Oct. 23, 2014, the entire contents of which are expressly incorporated by reference herein.

BACKGROUND OF THE INVENTION

1. Field of the Invention

The present invention relates in general to the field of eye protection, and, more particularly, to flip-to-wear eye shields.

2. Discussion of the Related Art

Protective eyewear usually covers the eye area in order to prevent particulates, infectious fluids, or chemicals, or light and other harmful rays such as ultraviolet (UV) radiation, lasers, and so on from striking the eyes. Commonly referred to as eye shields, protective eyewear comes in a variety of forms such as goggles, masks, glasses, etc. and is useful in a number of different activities to protect a user's eyes from harm. For example, protective eyewear is especially useful for splash protection in health and safety-related environments where the user's eyes may be exposed to chemicals, blood-borne pathogens or other potentially infectious materials (OPIM). Protective eyewear may also be used by workers in a construction zone to prevent harmful debris or other particles or materials from striking workers' eyes. Protective eye wear is also important in sports and other outdoor activities like bicycling, running or sunbathing where a user's eyes may need protection from wind, dust or other air-borne debris or from harmful light and ultraviolet (UV) rays.

Protective eyewear can be very expensive depending on the application. For example, cyclists use very expensive protective eyewear to protect their eyes from wind, sunlight and from dust and other debris striking a user's eyes at high speeds. A cyclist's protective eyewear can become damaged, lost or stolen and often has to be replaced on a regular basis, which can lead to significant expense due to the replacement value of the protective eyewear. Additionally, in certain industries eye shields may become contaminated or otherwise damaged after every use, which can lead to significant expense for eye shields with high replacement value. For example, eye shields used in a laboratory or emergency room environment may become contaminated due to exposure or potential exposure to OPIM.

As a result, certain eye shields are designed to be disposable after a single use. Disposable eye shields are useful in these cases since an eye shield may become contaminated or damaged during use and replacing the eye shield can be more cost-effective or practical than sterilizing a contaminated eye shield or repairing a damaged eye shield. In many eases it is safer and more time and cost efficient to simply discard the eye shields after use rather than attempt to disinfect or otherwise decontaminate them. Additionally, regulations may require protective eyewear to be disposable after a single use. For example, in an operating room environment it may be required by government regulations for users to dispose of their protective eyewear following surgery or other medical procedure.

Many eye shields on the market today are also fairly cumbersome and difficult to store due to having a relatively large profile. These eye shields usually consist of a static, right-angle lens and frame design which can be cumbersome to carry around when not in use and must be stored in specially designed cases that are also quite cumbersome based on their larger profiles. These eye shields may be designed to be folded and stored in a case and require cleaning or wiping to keep the lens area clean. Additionally, packaging and transporting eye shields to the point of sale can be very difficult because of their cumbersome profile in the static, right-angle lens and frame design. For example, eye shields for use in a laboratory or medical-related environments are often packaged and sold in a preassembled configuration so that they may be easily used right out of the package. However, preassembled eye shields are often cumbersome to store and transport because they are packaged and shipped in the preassembled configuration which requires a large amount of space in their storage and/or shipping containers. These containers may only store a limited number of disposable eye shields. In addition these containers may require more space than is practically available at the eye shield's point-of-use, such as in a medical treatment room.

U.S. Pat. No. 8,214,921, titled "Flip-to-wear eye shield," assigned to the present assignee and incorporated herein by reference in its entirety, discloses a flip-to-wear eye shield designed for efficient storage and ease of use. The eye shield may be dispensed in a compact, easy-to-assemble configuration in which one or more hinges allow a protective lens to pivot with respect to a frame from a first substantially flat position for compact storage to a second position ready for use. However, the eye shield requires the manufacture and assembly of multiple discrete components, including a protective lens, a frame and hinges which may clip or mount onto the frame. As a result, the eye shield requires increased time and cost to manufacture and assemble.

SUMMARY AND OBJECTS OF THE INVENTION

By way of summary, the present invention is directed to flip-to-wear eye shield with an improved design and/or fewer discrete components. By integrating the hinge into elements of the frame and/or the lens, an eye shield can be manufactured and assembled more quickly and with less costs.

In an embodiment, a lens may click (or snap) onto molded posts of a frame in a substantially flat position. An integrated living hinge in the frame may bend to allow the lens to flip downwards toward the frame to a second position for use. The posts may also click (or snap) into place in an underside of the frames.

In another embodiment, a lens may click (or snap) onto molded posts of a frame in a substantially flat position. An integrated living hinge, formed by notches in the lens, may allow the lens to bend to flip downwards toward the frame to a second position for use.

In accordance with a first aspect of the invention, these objects are achieved by providing an apparatus comprising: a flip-to-wear eye shield comprising: (a) a frame having: a body for wrapping around a user's head; and first and second tabs protruding from the body, a base connected to each tab, and a post connected to each base; and (b) a protective lens shaped to cover eyes of a user having: first and second notches; and first and second apertures in proximity to the first and second notches for receiving the posts of the frame.

In accordance with a second aspect of the invention, these objects are achieved by providing an apparatus comprising: a flip-to-wear eye shield comprising: a protective lens providing first and second apertures for coupling to a frame; and a frame comprising: (a) a body; (b) first and second tabs connected to the body; (c) a base connected to each of the first and second tabs to form an integrated living hinge between; and (d) a post connected to each base. The posts are configured to attach to the first and second apertures to retain the protective lens. In this embodiment, upon attachment, the protective lens lies substantially flat with respect to the frame in a first position for compact storage, and the integrated living hinge is operable to bend to allow the protective lens to pivot with respect to the frame in a second position for use.

In accordance with a third aspect of the invention, these objects are achieved by providing a method comprising: a flip-to-wear eye shield comprising: a protective lens comprising: (a) first and second apertures for coupling to a frame; and (b) notches in proximity to the first and second apertures; and a frame comprising: (a) a body; and (b) first and second posts coupled to the body, wherein the first and second posts are configured to attach to the first and second apertures of the protective lens, respectively. Upon attachment, the protective lens lies substantially flat with respect to the frame in a first position for compact storage, and the notches permit the protective lens to bend with respect to the first and second posts to allow the protective lens to pivot with respect to the frame in a second position for use.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

DESCRIPTION OF EMBODIMENTS

Figure 1:
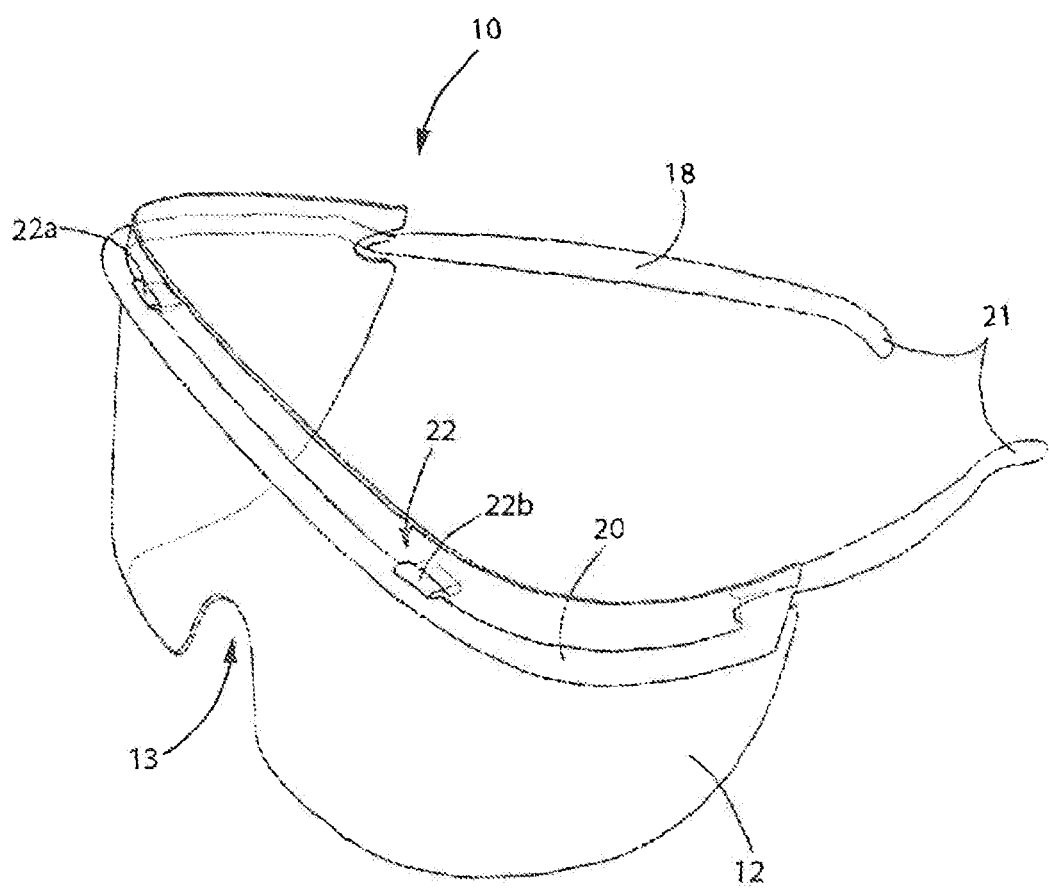
FIG. 1 is a perspective view of a flip-to-wear eye shield in a position for use in accordance with an embodiment of the present invention.

In describing the preferred embodiment of the invention, which is illustrated in the drawings, specific terminology will be resorted to for the sake of clarity. However, it is not intended that the invention be limited to the specific terms so selected and it is to be understood that each specific term includes all technical equivalents, which operate in a similar manner to accomplish a similar purpose. For example, the words "connected", "coupled", "attached", or terms similar thereto are often used. They are not limited to direct connection but include connection through other elements where such connection is recognized as being equivalent by those skilled in the art.

Specific embodiments of the present invention will now be further described by the following, non-limiting examples which will serve to illustrate various features of significance. The examples are intended merely to facilitate an understanding of ways in which the present invention may be practiced and to further enable those of skill in the art to practice the present invention. Accordingly, the examples should not be construed as limiting the scope of the present invention. Note the various inventive elements are shown in several views.

Beginning with FIG. 1, a perspective view of a flip-to-wear eye shield 10 in a position ready for use is provided in accordance with an embodiment of the present invention. The eye shield 10 comprises a protective lens (or other eye covering member) 12 coupled to a generally "U" shaped frame 18 configured to be worn similar to eye glasses. The protective lens 12 may be shaped to cover both eyes of a user when worn and include a nose area 13 for resting on the nose of a user.

The frame 18 comprises a body 20, which may be a single article manufactured from a thermoplastic polymer. Tabs 22, such as first and second tabs 22a and 22b, connected to the body 20 provide respective bases and posts that are configured for attachment to apertures or openings, such as first and second apertures, of the protective lens 12. Initially, upon attachment, the protective lens 12 lies substantially flat with respect to the frame 18 in a first position for compact storage. Accordingly, multiple eye shields 10 may be stacked in a container for efficient shipment and distribution. Then, upon retrieving a particular eye shield 10, an integrated living hinge of the eye shield 10 is operable to bend to allow the protective lens 12 to pivot with respect to the Frame 18 to a second position for use.

Figure 2:
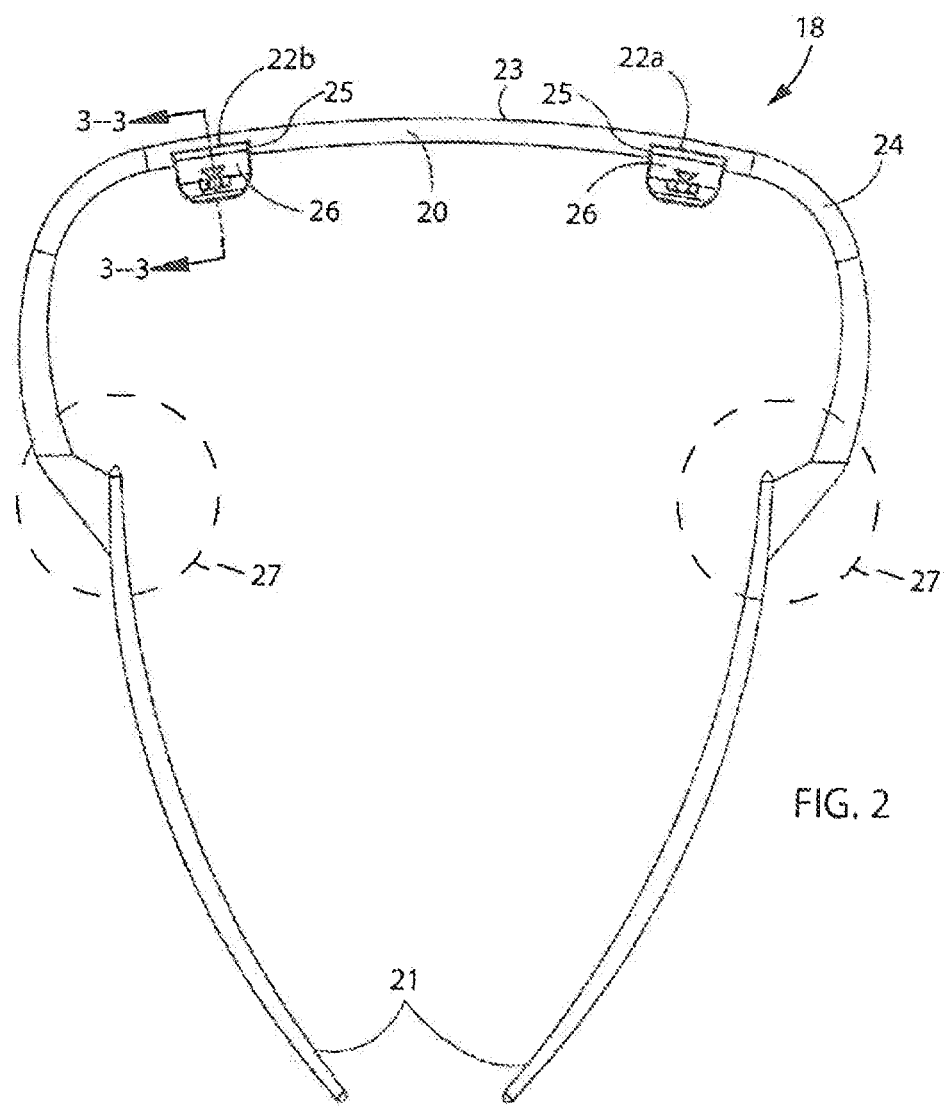
FIG. 2 is a plan view of a frame in accordance with an embodiment of the present invention.

Referring now to FIG. 2, a plan view of the frame 18 is provided in accordance with an embodiment of the present invention. The frame 18 includes tabs 22, such as first and second tabs 22a and 22b, in a front area of the frame 18 generally corresponding to above the eyes of a user. A base 26 is connected to each of the tabs 22 to form an integrated living hinge 25 between the base 26 and the tab 22. Alternative embodiments could provide a single tab and base arrangement on a frame, such as at the center of the frame 18, or an arrangement of multiple tabs and bases disposed around the frame.

Figure 4:
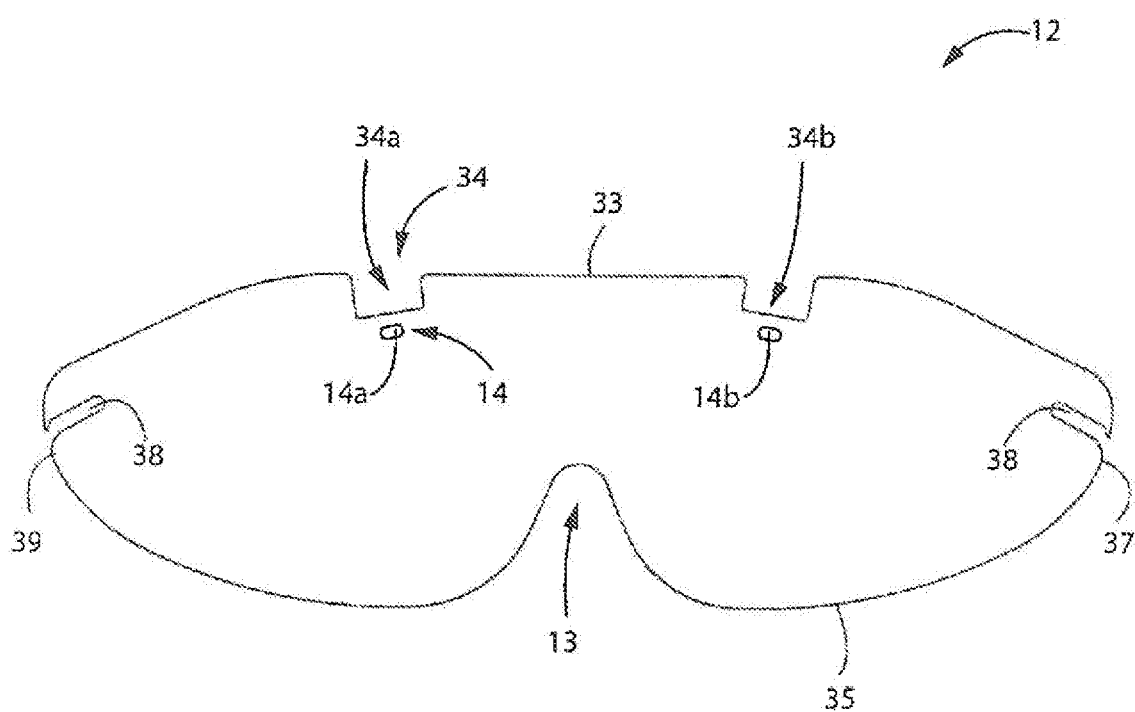
FIG. 4 is a front view of a protective lens in accordance with an embodiment of the present invention.

The frame 18 illustrates one embodiment comprising a plastic, composite, or metal rod or tube preferably made from a spring-like memory retaining material. In the illustrated embodiment, the frame 18 is bowed along its length to form a generally "U" shaped member extending from an area behind the user's ears and along the user's forehead. A forehead portion 23 is shaped to contour to a user's forehead and to bend around a temple area 24 to fit to the user's face. Opposite ends 21 are connected to the temple area 24 of the frame 18 with, for example, inward bends 27. These inward bends 27 are given by way of illustration and not of limitation as any known mechanism may be employed to connect the opposite ends 21 with the temple area 24 of the frame 18. In this embodiment, inward bends 27 are configured to align with cutaways of the lens, such as cutaways 38 of the lens 12 as shown in FIG. 4. The inward bends 27 align with the cutaways to provide areas for the cutaways to be locked into position. Once the cutaways are locked into the inward bends 27, the eye shield 10 is in the fully assembled position ready for wearing and use by a user. This locked position prevents the protective lens 12 from pivoting or otherwise moving relative to the frame 18.

The frame 18 is preferably of a length sufficient so that its two opposite ends 21 extend slightly beyond a user's ears and rest in the ear saddle when the eye shield is placed on the user's head. Where, as in the illustrated embodiment, a bowed or u-shaped frame is used, the location of the bends (or other connective mechanisms) may be chosen such that bends align with the notches of the lens 12 and lock into position.

Although a rigid frame 18 could be used, the frame 18 is preferably formed of a lightweight, spring-like material such as polyethylene; polypropylene or PVC which retains its memory to a first unsprung position, and which can be sprung to a second position when the frame 18 is placed on a user's head. In this second sprung position, the opposite ends 21 are urged or biased toward the original unsprung position under the influence of the lightweight, spring-like material. Such a feature, may assist in securing the frame 18 of the eye shield 10 on a user's head as the bowed frame 18 is biased toward the direction of the unsprung position.

Figure 3:
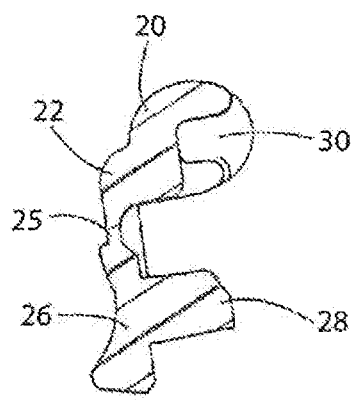
FIG. 3 is a sectional view of the frame of FIG. 2 taken along the line 3-3.

Referring now to FIG. 3, a sectional view of the frame of FIG. 2 taken along the line 3-3 illustrates an integrated living hinge 25 formed between the tab 22 and the base 26 in accordance with an embodiment of the present invention. The living hinge 25 is a thin, flexible portion of the plastic which may be repeatedly folded and integrally formed on the plastic itself. The living hinge 25 may be thinner than the tab 22 and/or the base 26, and may be integrally formed with the tab 22 and/or the base 26.

In operation, the configuration of the living hinge 25 may facilitate bending, or flexing downward, to allow the protective lens 12 to pivot with respect to the frame 18 into the second position for use. The living hinge 25 is an integrated connection area that is operable to bend to allow movement between two sides. For example, by pressing a finger to the base 26 downward with respect to the tab 22, the base 26 flexes downward with respect to the tab 22 (and downward with respect to the rest of the frame 18) at the living hinge 25. The living hinge 25 may be designed to accommodate bending or flexing multiple times. Alternatively, with disposability of the nip-to-wear eye shield 10 in mind, the living hinge 25 may be designed to accommodate bending or flexing only a few times, or perhaps one time, to expand the possibility materials for the protective lens 12.

A post 28 connected to the base 26 is configured to attach to an aperture or opening of the protective lens 12 to retain the protective lens 12 to the frame 18. The post 28 may be tapered circumferentially such that attachment of the protective lens 12 requires clicking (or snapping) the protective lens 12 onto the post 28 for positive retention. Pushing the base 26 down then operates to rotate the protective lens 12, which is attached to the post 28 on the base 26, inside the frame 18, pivoting the protective lens 12 with respect to the frame 18. In addition, upon flexing the base 26 downward at the living hinge 25, the post 28 may also be positively retained in position, such as by clicking (or snapping) the post 28 into a cavity 30 disposed in the frame 18 and similarly having a circumferentially tapered edge.

Referring now to FIG. 4, a front view of the protective lens 12 is provided in accordance with an embodiment of the present invention. The protective lens 12 is substantially transparent and flexible, and preferably made of a thin gauge material. Suitable materials may include polyester, polyvinyl chloride, polyethylene, polypropylene, polystyrene, polycarbonate, acetate, cellulosic, or acrylic plastic. The specific material used is not critical although a material which is optical grade, anti static coated and fog resistant is preferred, A preferred material may include a polyester resin such as commercially available Lexan® or a thermoplastic carbonate-linked polymer produced by reacting bisphenol-A and phosgene.

However, other plastics, as described above, may also be used, and since in at least certain embodiments are single use, disposable lenses; less expensive plastics may be quite suitable. A preferred plastic may also be relatively thin and commonly available in flexible sheets from which the protective lens 12 can be readily stamped or cut, without shattering, cracking, and so forth. The lens material is also preferably flexible so that it can be bowed to conform to a user's face without significant visual distortion. The lens may also be of a certain length such that, when secured in the frame 18, it extends over the eyes beyond the user's temples, thereby offering significant protection for the user's eyes from both the front and side directions with insignificant or virtually no visual distortion in the area of the bend or bow of the frame 18. Additionally, the protective lens 12 may be clear, polarized, or it may be treated for UV protection, tinted, smoked, mirrored, or coated for hardness. The protective lens 12 may also be non-reflective, anti-fogging, and the like.

In the illustrated embodiment of FIG. 4, the protective lens 12 includes apertures 14 for coupling to a frame. In a preferred embodiment, the protective lens 12 includes first and second apertures 14a and 14b in an area generally above the eyes of a user for attachment to posts on the frame 18. In addition, in proximity to apertures 14, the protective lens 12 may include notches 34, such as first and second notches 34a and 34b, configured to fit around the tabs and/or bases of the frame 18 for ease of assembly. The notches 34 may be angular or U-shaped cuts, indentations, or slits in the protective lens 12, in proximity to the apertures 14. The protective lens 12 may also include cutaways 38 on opposite ends of the protective lens 12 that are configured to fit on the body (arms) of the frame 18, such as at the inward bends 27, when in the second position ready for use.

The protective lens 12 extends between a pair of opposite side edges 37 and 39 which are separated at a distance such that the protective lens 12 extends as far as the users temples when the eye shield 10 is worn. In this embodiment, the upper edge 33 extends along the user's forehead, usually at or above the eyebrows, with a lower edge 35 extending down as far as the user's cheeks with nose area 13 resting on or extending slightly above the bridge of the user's nose. There may also be an optional cushion (not shown) in the form of an elongated piece or strip comprising foam, plastic, rubber, or preferably a lightweight sponge material having an adhesive along one or more surfaces. The cushion may be used to facilitate user comfort while wearing the eye shield 10, and could be placed along the upper edge 33 of the protective lens 12 so that it offers a pad between the protective lens 12 and the user's forehead.

Figure 5:
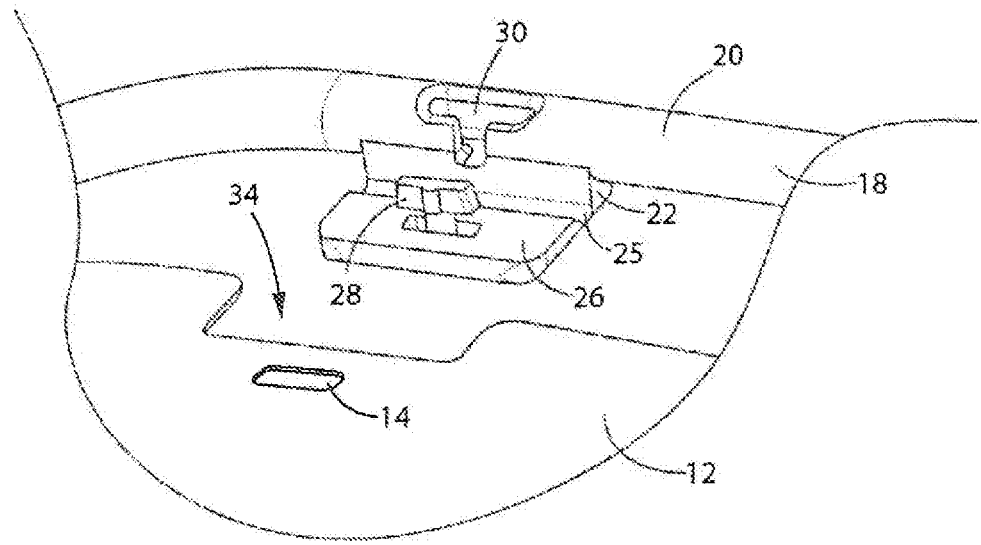
FIG. 5 is an underside perspective view of a protective lens and a frame, prior to attachment, in accordance with an embodiment of the present invention.

Referring now to FIG. 5, an underside perspective view of the protective lens 12 and the frame 18, prior to attachment, is provided in accordance with an embodiment of the present invention. Here, the protective lens 12 and the frame 18 are separate components that are joined together by the aperture 14 of the protective lens 12 snapping (or clicking) onto the post 28 of the frame 18. Also, the protective lens 12 is positioned over the topside of the frame 18.

Figure 6:
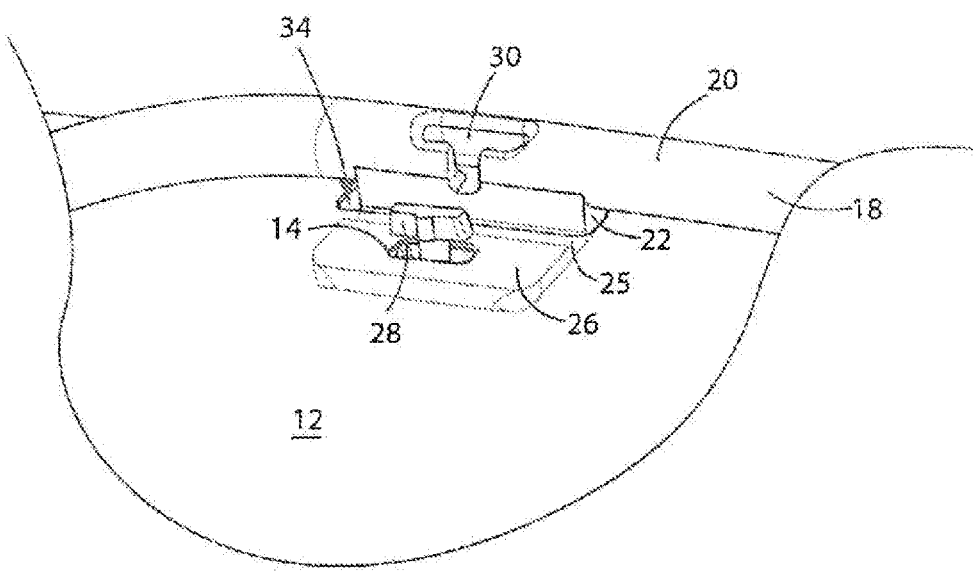
FIG. 6 is an underside perspective view of a protective lens and a frame, upon attachment, in accordance with an embodiment of the present invention.
Figure 7:
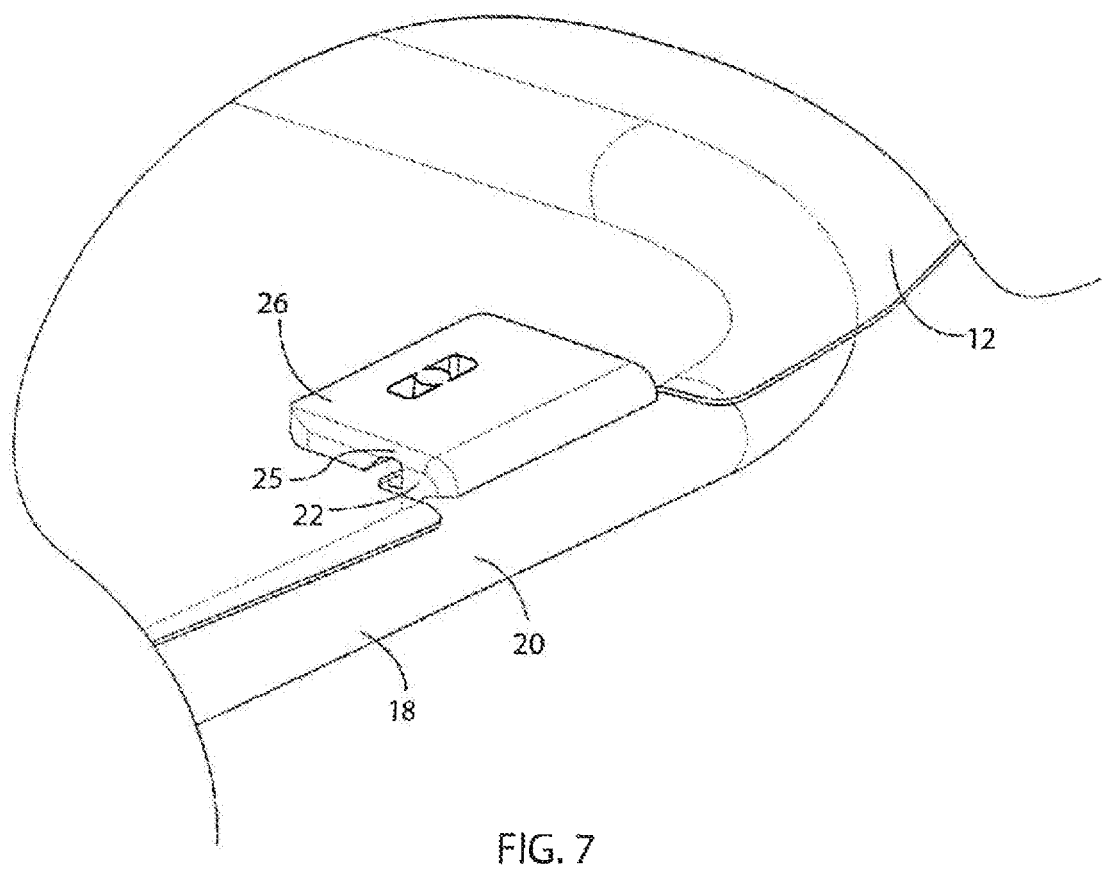
FIG. 7 is a topside perspective view of a protective lens and a frame, upon attachment, in accordance with an embodiment of the present invention.

Referring next to FIG. 6, upon attachment of the protective lens 12 to the post 28, the eye shield 10 is assembled in a first position that is substantially flat with respect to the frame for compact storage. The notch 34 in proximity to aperture 14 fits around the tab 22 and the base 26. Also, the protective lens 12 is still positioned over the topside of the frame 18, which can also be seen from a topside perspective view of in FIG. 7. To subsequently move to a second position for use, the living hinge 25 bends or flexes downward, such as by pressing down on the base 26 with a finger while holding the frame 18. The protective lens 12 then pivots with respect to the frame 18, via the living hinge 25, and the protective lens folds interior to the frame 18 with the cutaways 38 on opposite ends of the protective lens 12 locking on the inward bends 27 of the frame 18.

Figure 8:
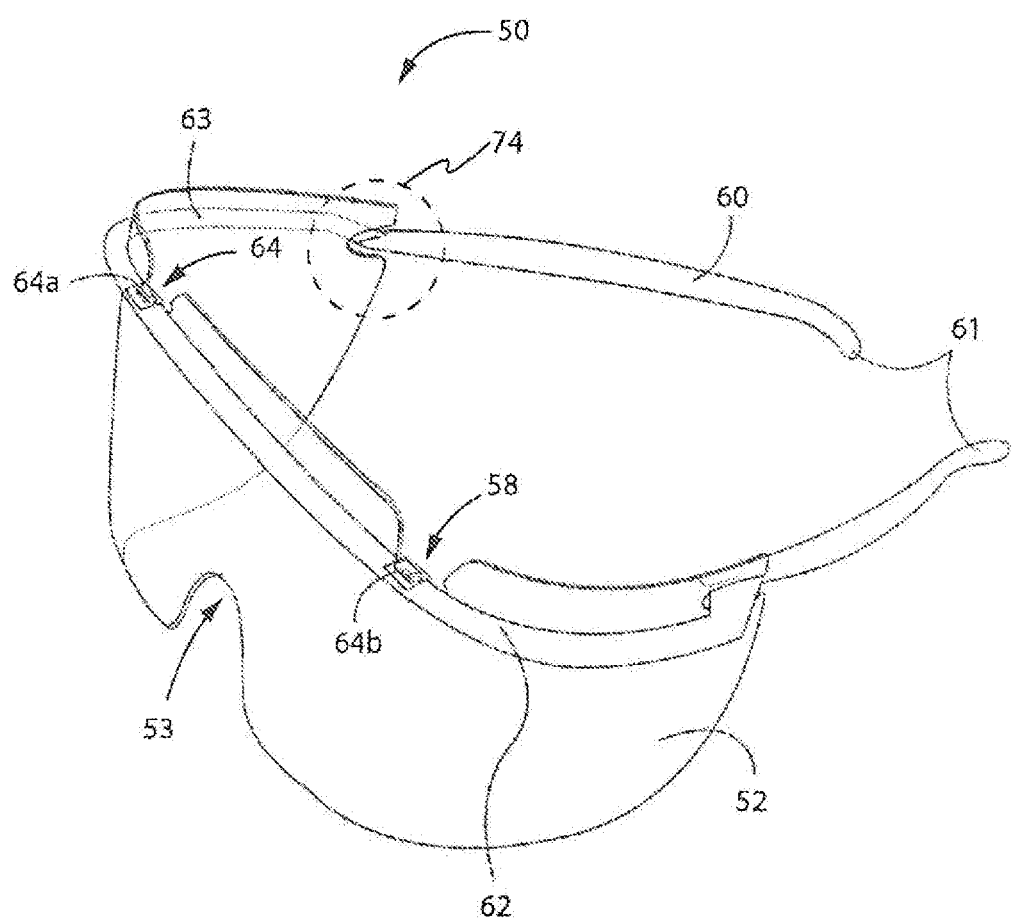
FIG. 8 is a perspective view of flip-to-wear eye shield in a position for use in accordance with another embodiment of the present invention.

Referring now to FIG. 8, a perspective view of a flip-to-wear eye shield 50 in a position far use is provided in accordance with another embodiment of the present invention. The eye shield 50 comprises a protective lens (or other eye covering member) 52 coupled to a generally "U" shaped frame 60 configured to be worn similar to eye glasses. Similar to the embodiment described above with respect to FIGS. 1 and 2, opposite ends 61 are connected to a temple area 63 of the frame 60 with, for example, inward bends 74. The protective lens 52 may be shaped to covet both eyes of a user when worn and include a nose area 53 for resting on the nose of a user.

Figure 9:
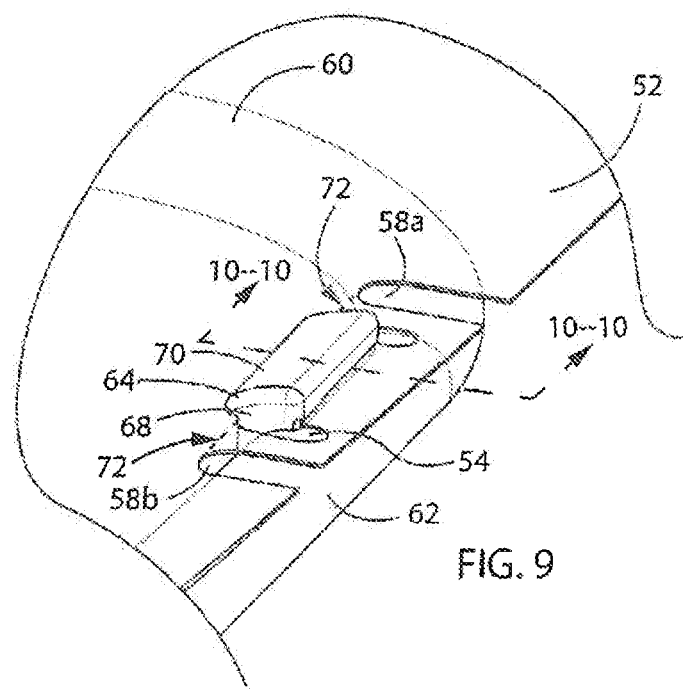
FIG. 9 is a topside perspective view of a protective lens and frame, upon attachment, of the eye shield of FIG. 8.

The frame 60 comprises a body 62, which may be a single article manufactured from a thermoplastic polymer. Posts 64, such as first and second posts 64a and 64b, connected to the body 62 are configured for attachment to apertures or openings, such as first and second apertures, of the protective lens 52 as shown in FIG. 9. Initially, upon attachment, the protective lens 52 lies substantially flat with respect to the frame 60 in a first position for compact storage. Accordingly, multiple eye shields 50 may be stacked in a container for efficient shipment and distribution. Then, upon retrieving a particular eye shield 50, an integrated living hinge of the eye shield 50 is operable to bend to allow the protective lens 52 to pivot with respect to the frame 60 to a second position for use.

Turning to FIG. 9, a topside perspective view of the protective lens 52 and the frame 60, upon attachment, of the eye shield of FIG. 8 is provided. Apertures 54, such as first and second apertures, are provided by the protective lens 52 for coupling to the frame 60. In particular, the protective lens 52 provides tabs 68 projecting from a body 62 of the frame 60. In turn, a base 70 connects to the tab 68, and the post 64 connects to the base 70. The posts 64 are configured to attach to an aperture (or opening) 54 of the protective lens 52 to retain the protective lens 52 to the frame 60. The post 64 may be tapered circumferentially around the base 70 such that attachment of the protective lens 52 requires clicking (or snapping) the protective lens 52 onto the post 64 for positive retention.

Figure 10:
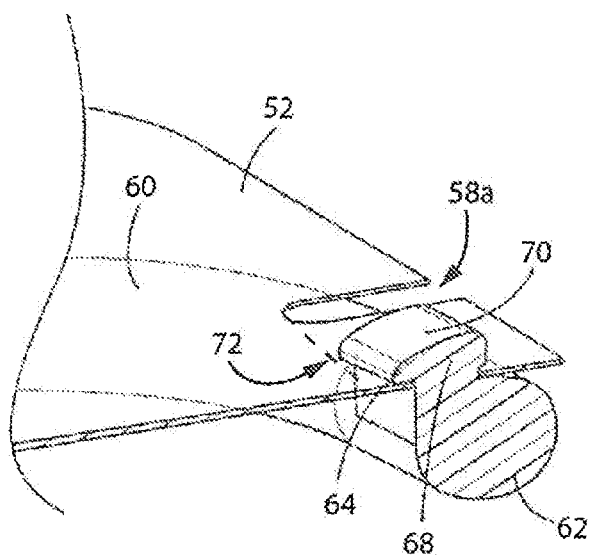
FIG. 10 is a sectional view of the lens and frame of FIG. 9 taken along the line 10-10.

Referring also to FIG. 10, a sectional view of the protective lens 52 and the frame 60 of FIG. 9 taken along the line 10-10 is provided. The protective lens 52 includes notches 58 in proximity to the apertures 54, such as a first notch 58a on a first side adjacent the aperture 54 and a second notch 58b on a second side adjacent the same aperture 54. The notches 58 may be angular or U-shaped cuts, indentations, or slits in the protective lens 52, in proximity to the apertures 54. The protective lens 52 also includes an area 72 that is operable as an integrated living hinge. The living hinge 72 may be designed to accommodate bending or flexing multiple times. Alternatively, with disposability of the flip-to-wear eye shield 50 in mind, the living hinge 72 may be designed to accommodate bending or flexing only a few times, or perhaps one time, to expand the possibility materials for the protective lens 52. Accordingly, pushing the protective lens 52 down then operates to rotate the protective lens 12, which is attached to the post 64 on the base 70, inside the frame 60, pivoting the protective lens 52 with respect to the frame 60.

Similar to the embodiments described above with respect to FIGS. 1-7, inward bends 74 on opposite ends of the frame 60 are configured to align with the notches of the protective lens 52. The inward bends 74 align with the cutaways on opposite ends of the protective lens 52 to provide areas for locking the protective lens 52 into position. Once the cutaways are locked into the inward bends 74, the eye shield 50 is in the fully assembled position ready for wearing and use by a user. This locked position prevents the protective lens 52 from pivoting or otherwise moving relative to the frame 60. The inward bends 74 are given by way of illustration and not of limitation.

Accordingly, the protective lens 52 may lie substantially flat with respect to the frame 60 in a first position for compact storage. In addition, the notches 58 permit the protective lens 52 to bend with respect to the posts 64 to allow the protective lens 52 to pivot with respect to the frame 60 in a second position ready for use.

Figure 11:
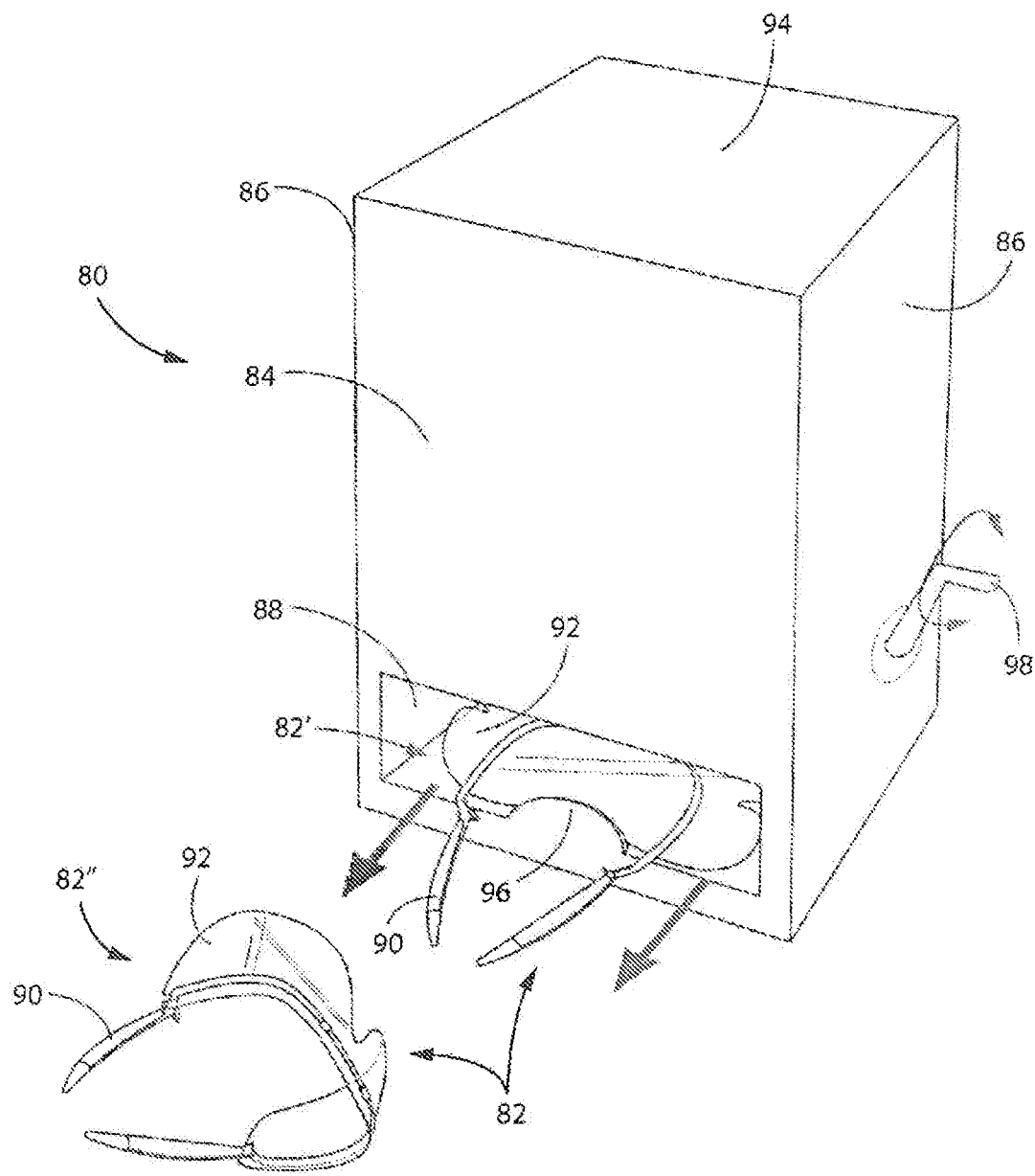
FIG. 11 is perspective view of a dispenser in which flip-to-wear eye shields may be stored substantially flat in a first position for compact storage and dispensed in a second position ready for use in accordance with an embodiment of the present invention.

Referring now to FIG. 11, a perspective view of a dispenser 80 in which flip-to-wear eye shields 82 may be stored substantially flat in a first position 82' for compact storage and dispensed in a second position 82" ready for use is provided in accordance with an embodiment of the invention. The dispenser 80 includes a housing having a front panel 84 and sidewalls 86 defining an interior volume configured to hold a plurality of flip-to-wear eye shields 82 in the first position 82'. The dispenser 80 also includes an opening 88 for dispensing. The opening 88 may be advantageously positioned in a lower portion of the front panel 84 to take advantage of gravity for feeding the flip-to-wear eye shields 82 downward upon dispensing. Accordingly, the dispenser 80 may store plurality of flip-to-wear eye shields 82 and may itself be conveniently shipped and stored.

In operation, an individual flip-to-wear eye shield 82 from among the plurality of flip-to-wear eye shields 82 may be exposed via the opening 88. The individual flip-to-wear eye shield 82 may comprise a frame 90 attached to a protective lens 92, such as in accordance with embodiments of the invention as described above with respect to FIGS. 1-10. In the first position 82' for compact storage, the frame 90 may be folded with respect to the protective lens 92, i.e., in a substantially flat position, to maximize the amount of flip-to-wear eye shields 82 that may be stored in the dispenser 80.

Upon removal of the individual flip-to-wear eye shield 82 from the dispenser 80 via the opening 88, a mechanism may facilitate rotation between the frame 90 and the lens 92 to move the flip-to-wear eye shield 82 into the second position 82" ready for use. The mechanism may include, for example, a compression force acting on the flip-to-wear eye shields 82 within the inferior volume of the dispenser 80 to prevent rotation while stored, such as by weight of the plurality of flip-to-wear eye shields 82, gravity and/or a spring pushing downward below a top 94 of the dispenser 80, and/or limiting of the size of the opening 88 to allow rotation simultaneous with, or subsequent to, removal of the individual flip-to-wear eye shield 82 at the opening 88. In some embodiments, a detent 96 in the opening 88 may push the lens 92 open (into the second position ready for use) as the individual flip-to-wear eye shield 82 is pulled out of the dispenser 80. In some embodiments, a mechanical lever 98, may also be disposed external to the dispenser 80 be allow rotation by a user to actuate one or more gears within the dispenser 80 to push the lens 92 open (into the second position ready for use) while dispensing an individual flip-to-wear eye shield 82. To other embodiments, the lens 92 may simply rest in closed position and may be manually opened after being dispensed.

Following removal of the individual flip-to-wear eye shield 82, a next individual flip-to-wear eye shield 82 from among the plurality of flip-to-wear eye shields 82 in the dispenser 80 may then be exposed via the opening 88. In other words, as each flip-to-wear eye shield 82 is removed from the dispenser 80, the dispensed flip-to-wear eye shield 82 may flip vertically into a normal position for wear while a next flip-to-wear eye shield 82 may be presented.

In some embodiments, the dispenser 80 may be refilled with more flip-to-wear eye shields 82, such as via the sidewalls 86 or the top 94, and/or the dispenser 80 may be permanently installed on a vertical support, such as a wall, either directly or by a separate retaining mechanism, including as described in co-pending U.S. patent application Ser. No. 14/213,416, titled "Dispenser-Packaging for Protective Eyewear," assigned to the present assignee and incorporated herein by reference in its entirety. In addition, other advantageous modifications may be made to the flip-to-wear eye shield 82 and/or the dispenser 80 within the scope of the present invention, including as described in co-pending U.S. patent application Ser. No. 14/209,567, titled "System and Method for Protective Eyewear, Dispensing," assigned to the present assignee and incorporated herein by reference in its entirety. For example, the flip-to-wear eye shields 82 may include an RFID transponder; the dispenser 80 may include a scanner and/or an electrical display; and so forth.

Throughout the foregoing specification, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. When a particular feature, structure, or characteristic is described in connection with an embodiment, it is submitted that it is within the knowledge of one skilled in the art to bring about such a feature, structure, or characteristic in connection with other embodiments whether or not explicitly described. Various changes may be made in the structure and embodiments shown herein without departing from the principles of the invention. Further, features of the embodiments shown in various figures may be employed in combination with embodiments shown in other figures.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept.

It should be appreciated that the individual components need not be formed in the disclosed shapes, or assembled in the disclosed configuration, but could be provided in virtually any shape and assembled in virtually any configuration. It is intended that the appended claims cover all such additions, modifications, and rearrangements. Expedient embodiments of the present invention are differentiated by the appended claims.

What is claimed is:

1. A flip-to-wear eye shield comprising:
    a protective lens providing an aperture; and
    a frame comprising:
    (a) a body;
    (b) a tab connected to the body;
    (c) a base connected to the tab to form an integrated living hinge between; and
    (d) a post connected to the base, wherein the post is configured to attach to the aperture to retain the protective lens,
    (e) a notch that is distinct and separate from the aperture;
    wherein the notch in the protective Hens in spaced proximity to the aperture, wherein the notch is configured to fit around the lab;
    wherein the aperture is configured for coupling to the frame; and
    wherein, upon attachment, the protective lens lies substantially flat with respect to the frame in a first position for compact storage, and the integrated living hinge is operable to bend to allow the protective lens to pivot with respect to the frame in a second position for use.

2. The flip-to-wear eye shield of claim 1, further comprising a cavity in the frame configured to retain the post in the second position.

3. The flip-to-wear eye shield of claim 1, wherein the living hinge is operable to bend by pressing a finger to the base.

4. The flip-to-wear eye shield of claim 1, wherein the protective lens is shaped to cover both eyes of a user.

5. The flip-to-wear eye shield of claim 1, further comprising first and second cutaways on opposite ends of the protective lens, wherein the first and second cutaways are configured to fit on arms of the frame in the second position.

6. The flip-to-wear eye shield of claim 1, wherein the integrated living hinge is thinner than the base.

7. The flip-to-wear eye shield of claim 6, wherein the integrated living hinge is integrally formed with the base.

8. The flip-to-wear eye shield of claim 6, wherein the protective lens provides a second aperture; and
the frame comprises:
a second tab connected to the body,
a second base connected to the second tab to form an integrated living hinge between, and
a post connected to the second base.

9. The flip-to-wear eye shield of claim 1, wherein the frame is a single article manufactured from a thermoplastic polymer.

10. A flip-to-wear eye shield comprising:
a protective lens shaped to cover both eyes of a user comprising:
(a) first and second apertures for coupling to a frame; and
(b) first and second notches in proximity to the first and second apertures; and
a frame comprising:
(a) a body;
(b) first and second tabs flexibly connected to the body;
(c) a base connected to each of the first and second tabs to form an integrated living hinge between; and
(c) a post connected to each base, wherein the posts are attached to the first and second apertures of the protective lens, respectively; and
(d) first and second cavities,
(e) wherein the first and second notches are distinct and separate from the first and second apertures;
wherein the first and second notches in the protective lens are in spaced proximity to the first and second apertures, wherein the first and second notches are configured to fit around the first and second tabs;
wherein the protective lens lies substantially flat with respect to the frame in a first position for compact storage, and the integrated living hinge is operable to bend to allow the protective lens to pivot with respect to the frame in a second position for use, and
wherein the first and second cavities retain the posts in the second position.

11. The flip-to-wear eye shield of claim 10, wherein the tabs are operable to bend by pressing a finger to the base.

12. The flip-to-wear eye shield of claim 10, further comprising first and second cutaways on opposite ends of the protective lens, wherein the first and second cutaways are configured to fit on arms of the frame in the second position.

13. The flip-to-wear eye shield of claim 10, wherein the integrated living hinge is thinner than the base and the integrated living hinge is integrally formed with the base.

* * * * *